US00PP32939P2

(12) United States Plant Patent
Hansen

(10) Patent No.: US PP32,939 P2
(45) Date of Patent: Mar. 30, 2021

(54) **X *MANGAVE* PLANT NAMED 'LIFE ON MARS'**

(50) Latin Name: **x *Mangave* hybrid**
Varietal Denomination: Life on Mars

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,337

(22) Filed: Mar. 23, 2020

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ... A01H 5/12; A01H 5/02; A01H 6/12; A01H 6/00; A01H 1/02; A01H 5/00
See application file for complete search history.

(56) References Cited

U.S. PATENT DOCUMENTS

PP32,041 P2 * 8/2020 Hansen ..... Plt./373

* cited by examiner

*Primary Examiner* — June Hwu

(57) ABSTRACT

A new and unique x *Mangave* plant named 'Life on Mars' characterized by a medium, rounded mound of fleshy, linear to lanceolate leaves that are slightly arching margins and develop glaucous, blue-green with lighter greenish-white to creamy yellow margins and developing bright reddish-purple splotches of variable sizes with high ultraviolet light. The leaves have numerous small, semi-flexible marginal teeth. The new plant is suitable for the garden or as a potted plant in the garden or home.

1 Drawing Sheet

Botanical classification: x *Mangave* hybrid.
Variety denomination: 'Life on Mars'.

STATEMENT REGARDING PRIOR DISCLOSURES UNDER 37 CFR 1.77(B)(6)

No plants of x *Mangave* 'Life on Mars' have been sold, in this country or anywhere in the world, nor has any disclosure of the new plant been made as of the filing of this application.

BACKGROUND OF THE INVENTION

The present invention relates to the new and distinct x *Mangave* hybrid plant, x *Mangave* 'Life on Mars' that was discovered by the inventor at a wholesale perennial nursery in Zeeland, Mich., USA as a whole plant mutation of 'Mission to Mars' U.S. Plant Pat. No. 29,393 in a batch of tissue culture propagated plants. The new plant was discovered on Jun. 14, 2019. Through trials at the same nursery the plant was assigned the code 19-SP-MANG-851-Q. The new plant has been successfully asexually propagated by sterile shoot-tip tissue culture and by basal offsets at the same nursery in Zeeland, Mich. The asexual tissue culture propagation has been found to produce stable and identical plants that maintain all the unique characteristics of the original plant.

BRIEF SUMMARY OF THE INVENTION x *Mangave* 'Life on Mars' differs from its parents as well as all other *Manfreda, Agave* and x *Mangave* known to the applicant. The parent lacks the lighter margin of the leaves.

The nearest comparison plants with variegation are: 'Kaleidoscope' U.S. Plant Pat. No. 28,614, 'Navajo Princess' U.S. Plant Pat. No. 31,136, 'Pineapple Punch' U.S. Plant patent application Ser. No. 16/602,654 and 'Snow Leopard' U.S. Plant Pat. No. 31,137. 'Kaleidoscope' has leaves that are thinner, narrower, less arching, and the marginal variegation is more yellowish with fewer and smaller reddish purple spots. 'Navajo Princess' has more stiff, folded leaves with margins that are more creamy-white, and the foliage is more glaucous blue with fewer and smaller greyed reddish-purple spotting. 'Pineapple Punch' is more upright in habit with shorter leaves having a more yellowish margin and smaller, less-intense, greyed reddish-purple blotching. 'Snow Leopard' has narrower, less arching leaves with margins that are more white, and the foliage is more glaucous blue with fewer and smaller greyed reddish-purple spotting.

'Life on Mars' is unique from all of the above cultivars and all *Agave*, x *Mangave* and *Manfreda* known to the inventor by the following combined traits:

1. Medium, rounded mound of linear to lanceolate, slightly arching, sarcous leaves;
2. Leaves are bluish-green and have a variegated lighter margin with greenish-white to creamy yellow in lower light intensity and developing bright reddish-purple splotches with higher ultraviolet intensity;
3. Leaf margins have many, small-sized, semi-flexible, marginal teeth;
4. Moderate to rapid growth rate;

BRIEF DESCRIPTION OF THE DRAWING

The photograph of x *Mangave* 'Life on Mars' demonstrates the overall appearance of the new plant including the unique traits as a nine-month-old plant grown in a greenhouse under low ultraviolet light in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
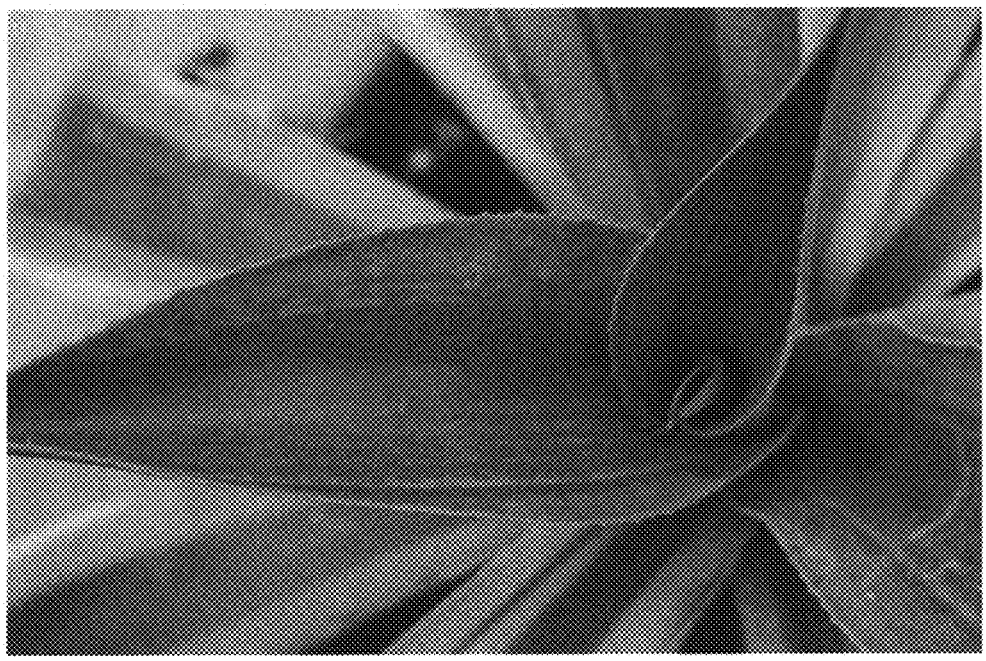
FIG. 1 shows the young foliage with marginal teeth from above.
Figure 2:
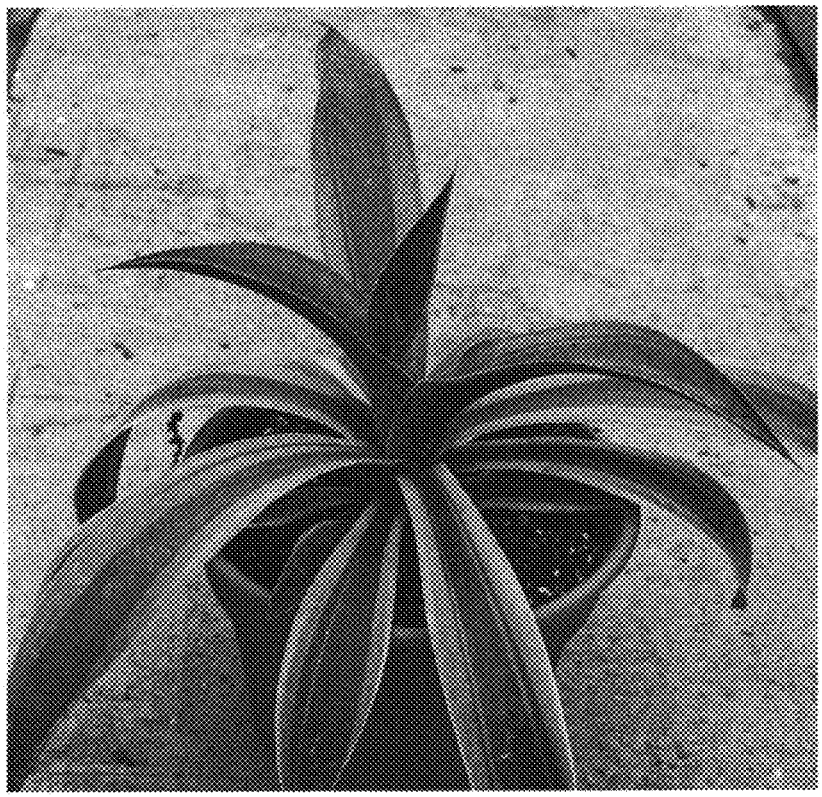
FIG. 2 shows a side view.

The following descriptions and color references are based on the 2015 edition of The Royal Horticultural Society Colour Chart except where common dictionary terms are used. The new plant, x *Mangave* 'Life on Mars', has not been observed under all possible environments. The phenotype may vary slightly with different environmental conditions, such as temperature, light, fertility, moisture and maturity levels, but without any change in the genotype. The following observations and size descriptions are of a nine-month-old plant in a commercial wholesale greenhouse in Zeeland, Mich. with supplemental water and fertilizer as needed.

Parentage: An uninduced whole plant sport of 'Mission to Mars';

Propagation: By sterile shoot-tip tissue culture;

Time to initiate roots from tissue culture: About three weeks;

Growth rate: Moderate to rapid;

Crop time: About 16 to 20 weeks to finish in a 3.8 liter container from a 35 mm tissue culture growing at about 21° C.;

Rooting habit: Fleshy, lightly branching, with roots up to 20 cm long;

Root color: Nearest RHS 158B;

Plant shape and habit: Succulent herbaceous perennial with basal rosettes of about 18 leaves radially emerging and slightly arching from central stem, producing a radially-symmetrical, rounded mound;

Plant size: Foliage height about 19.0 cm tall from soil line to the top of the leaves and about 38.0 cm wide at the widest point just above soil level;

Stem: To about 2.5 cm across; covered with foliage;

Foliage description: Linear to lanceolate; simple; sessile; bi-laterally symmetrical; sarcous; apex narrowly acute with terminal spine; base truncate and clasping; margins flat; serrate with small, flexible, outwardly pointing teeth; both adaxial and abaxial glabrous and glaucous, becoming lustrous adaxial;

Leaf size: To about 29.0 cm long, about 55.0 mm wide toward middle, about 3.5 cm wide at base; and about 5.0 mm thick; spotting variable sizes from 4.0 mm diameter to overlapping and nearly solid in high intensity ultraviolet light;

Variegation: Adaxial to about 18.0 mm wide in middle; abaxial to about 6.0 mm wide;

Leaf blade color:

*Adaxial margin* (*low light*).—Blend between RHS 144D and RHS 145D in perimeter half and interior half nearest blend between RHS N138D and RHS 145D with faint overtone spots nearest RHS 180B.

*Adaxial center* (*low light*).—Darker than RHS 139A with faint spots of nearest RHS 183D.

*Abaxial margin* (*low light*).—Nearest blend between RHS 138C and RHS 138B, typically without spots.

*Abaxial center* (*low light*).—Darker than RHS 139A with midrib nearest 138A without spots.

*Adaxial margin* (*high light*).—Blend between RHS 139C and RHS 139D with spots to near solid sections nearest RHS N186C.

*Adaxial center* (*high light*).—Nearest RHS N138A with spots to near solid sections nearest RHS N186C.

*Abaxial margin* (*high light*).—Nearest RHS 138B with spots nearest RHS 183A.

*Abaxial center* (*high light*).—Nearest RHS 139A with spots nearest RHS N186C and surrounding midrib nearest RHS 138A.

Foliage fragrance: None observed;

Apical spine: About 8.0 mm long and 1.0 mmm wide; semi-flexible; color nearest RHS 200B;

Marginal teeth: Small, semi-flexible; protruding about 1.0 mm long from margin and 1.0 mm wide at base, average spacing about 2.8 mm apart; color variable, nearest RHS 157D to RHS 164B on young leaves and nearest RHS 165A mature leaves;

Petiole: Leaves sessile;

Veins: Parallel; not distinct abaxial or adaxial;

Flower description: Not yet observed;

Fruit and seed not observed;

Disease resistance: X *Mangave* 'Life on Mars' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Life on Mars' as herein described and illustrated.

* * * * *